(12) United States Patent
Celeste

(10) Patent No.: US 11,039,707 B2
(45) Date of Patent: Jun. 22, 2021

(54) MICROENCAPSULATED DELIVERY SYSTEM

(75) Inventor: Salvatore Albert Celeste, Peabody, MA (US)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 875 days.

(21) Appl. No.: 12/947,552

(22) Filed: Nov. 16, 2010

(65) Prior Publication Data
US 2011/0177141 A1 Jul. 21, 2011

Related U.S. Application Data

(63) Continuation-in-part of application No. PCT/US2009/040710, filed on Apr. 15, 2009, and a
(Continued)

(51) Int. Cl.
| | |
|---|---|
| *A47J 31/08* | (2006.01) |
| *B65D 85/816* | (2006.01) |
| *A61K 8/02* | (2006.01) |
| *A47G 19/22* | (2006.01) |
| *A61K 8/11* | (2006.01) |
| *A61Q 19/00* | (2006.01) |
| *A47J 31/00* | (2006.01) |
| *A61K 8/67* | (2006.01) |
| *B65D 85/808* | (2006.01) |

(Continued)

(52) U.S. Cl.
CPC .............. *A47J 31/08* (2013.01); *A23L 27/72* (2016.08); *A23P 10/30* (2016.08); *A47G 19/2205* (2013.01); *A47J 31/002* (2013.01); *A61K 8/0208* (2013.01); *A61K 8/11* (2013.01); *A61K 8/671* (2013.01); *A61Q 19/00* (2013.01); *B65D 85/808* (2013.01); *B65D 85/816* (2013.01); *A61K 2800/412* (2013.01)

(58) Field of Classification Search
CPC .................................................. A23L 1/22016
USPC ............................................................ 426/78
See application file for complete search history.

(56) References Cited

U.S. PATENT DOCUMENTS

| | | |
|---|---|---|
| 3,173,878 A | 3/1965 | Reyes |
| 3,516,941 A | 6/1970 | Matson |

(Continued)

FOREIGN PATENT DOCUMENTS

| | | |
|---|---|---|
| EP | 0 393 289 A1 | 10/1990 |
| JP | 2000157418 | 6/2000 |

(Continued)

OTHER PUBLICATIONS

International Search Report for International Application PCT/US09/40710, dated Jun. 10, 2009.
(Continued)

*Primary Examiner* — Erik Kashnikow
*Assistant Examiner* — Lela S. Williams
(74) *Attorney, Agent, or Firm* — Licata & Tyrrell P.C.

(57) ABSTRACT

A microencapsulated delivery system, composition or method is disclosed in which one or more agents to be delivered are encapsulated in small capsules (e.g., microcapsules), and the capsules are applied or adhered to one or more surfaces of a substrate. The encapsulated agent is latently released upon exposure to appropriate conditions.

5 Claims, 9 Drawing Sheets

Related U.S. Application Data continuation-in-part of application No. 12/121,809, filed on May 16, 2008, now abandoned.

(60) Provisional application No. 60/930,586, filed on May 17, 2007.

(51) Int. Cl.
*A23L 27/00* (2016.01)
*A23P 10/30* (2016.01)

(56) References Cited

U.S. PATENT DOCUMENTS

| | | | |
|---|---|---|---|
| 4,904,524 A | 2/1990 | Yoh | |
| 5,356,647 A | 10/1994 | Mason et al. | |
| 5,603,953 A | 2/1997 | Herbig et al. | |
| 7,090,869 B2 | 8/2006 | Ohmachi et al. | |
| 2002/0168580 A1 | 11/2002 | Kubota et al. | |
| 2002/0195355 A1 | 12/2002 | Dennen | |
| 2005/0061733 A1* | 3/2005 | Bentz et al. | 210/491 |
| 2005/0089548 A1 | 4/2005 | Virgalitto et al. | |
| 2005/0186256 A1 | 8/2005 | Dihel | |
| 2007/0042184 A1 | 2/2007 | Coyne | |
| 2007/0148198 A1 | 6/2007 | Joseph | |
| 2007/0148459 A1 | 6/2007 | Wael et al. | |
| 2007/0202184 A1 | 8/2007 | Amundson et al. | |
| 2008/0102191 A1 | 5/2008 | Munt et al. | |
| 2010/0316768 A1 | 12/2010 | Stillman | |
| 2011/0008498 A1 | 1/2011 | Ribi | |

FOREIGN PATENT DOCUMENTS

| | | | | |
|---|---|---|---|---|
| WO | WO2000057713 | * | 3/2000 | |
| WO | WO 2003/043659 | | 5/2003 | |
| WO | WO 2005/018794 | * | 5/2005 | B01J 13/04 |
| WO | WO 2007/075216 A1 | | 7/2007 | |

OTHER PUBLICATIONS

Supplementary Partial European Search Report for EP 09747104, dated Jan. 7, 2015.

* cited by examiner

MICROENCAPSULATED DELIVERY SYSTEM

RELATED APPLICATIONS

This application is a continuation-in-part application of U.S. patent application Ser. No. 12/121,809, filed May 16, 2008, which claims the benefit of U.S. Provisional Application Ser. No. 60/930,586, filed May 17, 2007. The entire teachings of the above applications are incorporated herein by reference.

BACKGROUND OF THE INVENTION

There are many applications in which it would be useful to have a safe, simple and reliable means for latent release of agents into the environment, such as into a liquid or high moisture environment. There are many examples of applications in the pharmaceutical, food, cosmetic, and analytical industries in which such a release or delivery system would be useful.

For example, various methods have been developed for the preparation of "instant" beverages or the subsequent addition of flavorings or other ingredients after the beverage has been prepared. Automatic drip coffee makers heat and regulate the passage of water through a permeable filter containing the ground coffee bean solids, while simultaneously imparting the extracted oils and flavors of the fractionated coffee bean into the water flow, thus creating a coffee-flavored beverage. Similarly, when preparing tea a bag or envelope of filter material is used to contain the leaf solids while the flavor is extracted from the ground tea leaf while being steeped in hot water. Currently, if additional flavoring such as a spice or herb is desired, one must purchase a pre-flavored quantity of the desired preparation or attempt to add the ingredient after brewing. Further, if one desires a premium flavor or more full-bodied roast, a quantity of that blend must be purchased as well. These additives and premium roasts are expensive and tend to have limited shelf-life, often spoiling before the purchased quantity can be reasonably consumed by an individual. Accordingly, it would be desirable to have a convenient means by which a beverage could be prepared in its entirety or additional additives could be imparted to a pre-existing beverage which are individually portioned and shelf-stable.

SUMMARY OF THE INVENTION

The invention relates generally to a unique, printable, microencapsulated delivery system/composition and to the use of the delivery system for the delivery of agents, including but not limited to, flavorings, pharmaceuticals, herbal remedies, medicinal preparations, cosmetics, analytical indicators, and food and beverage additives. The invention also relates to methods of manufacturing the microencapsulated delivery system of the invention.

In one embodiment the invention provides a convenient means by which a beverage may be prepared in its entirety or additional additives may be imparted to a pre-existing beverage utilizing latent release of microencapsulated ingredients that provide additional desirable characteristics to the beverage when the microcapsules are combined with, or otherwise contacted by, a fluid. Additional additives could be, for example, flavorings, minerals, vitamins, condiments, colorings, herbs, spices or medicinal ingredients. In another embodiment the invention provides a method of "instant" preparation of a variety of beverage components in which the primary constituents of a beverage are encapsulated in a delivery system of the invention; when water or other appropriate liquid is introduced into the system, the fluid dissolves the microcapsules, releasing the constituent components into the solvent and creating a new beverage instantly.

Other exemplary embodiments of the invention are encompassed which, while maintaining the same design features and physical characteristics, can be applied to entirely different applications. For example, microencapsulated delivery systems of the invention can be used to enhance the utility and convenience of use of many medicinal preparations such as vaccines and pharmaceuticals, as well as a variety of analytical indicators such as those employed for urinalysis and pregnancy testing. Additional exemplary embodiments are) encompassed relating to the sanitizing or removal of undesirable compounds in liquids, including, but not limited to, the removal of microorganisms by means of latent release of antimicrobials to make impure water potable and/or the removal of chemical compounds such as chlorine from water utilizing the latent introduction of chlorine scavengers such as potassium nitrate or lithium carbonate to improve taste. Other embodiments are also included, such as binary adhesives (e.g., two-part epoxies and binary disinfectants) that require latent activation.

Accordingly the invention relates to a microencapsulated delivery system/composition or method in which one or more agents to be delivered are encapsulated in small capsules (e.g., microcapsules), and the capsules are adhered to one or more surfaces of a substrate. To effect delivery of the agent(s), the substrate and/or capsules are subjected to conditions (e.g., tactile pressure, pH change, temperature change, contacted with a chemical or contacted with a fluid or high moisture environment) such that the encapsulated agent(s) are substantially released from the capsule. The invention also relates to specific embodiments of the microencapsulated delivery system in the form of cups, bags, filters, flavor discs, cosmetic applicators, etc.

The invention further relates to methods of making the microencapsulated delivery system comprising encapsulating one or more agents to be delivered in microcapsules, and applying the encapsulated agent(s) to a substrate.

In one embodiment the invention relates to a composition comprising a substrate having adhered thereto one or more microcapsules comprising one or more polymers encapsulating one or more agents to be delivered, such that said one or more agents to be delivered are released upon exposure to appropriate conditions. In one embodiment said appropriate conditions excludes tactile breakage of the microcapsules. In one embodiment, appropriate conditions comprise one or more specific matching conditions. In another embodiment appropriate conditions comprise a chemical reaction involving the microcapsule and the substrate or environment.

In particular embodiments the substrate is selected from the group consisting of paper, waxed paper, plastic, glass, styrene, fiber, filter paper, tea bags, coffee flavor pods and discs and aluminum foil. In other embodiments the one or more agents to be delivered are selected from the group consisting of one or more flavorings, aromas, fragrances, colorings, pharmaceuticals, herbal remedies, vitamins, minerals, medicinal preparations, cosmetics, cosmetic agents, chemical agents, analytical agents, food additives, and beverage additives. In some embodiments the one or more polymers are selected from the group consisting of natural or synthetic polymers, gums, starches, lipids, pectins, and agars. In some embodiments the composition is a beverage filter, beverage flavor disc, cosmetic applicator, cosmeceutical applicator, cooking bag, flavor cup, indicator cup, pharmaceutical delivery cup, or water safety cup.

The invention also relates to a method of preparing a composition comprising admixing one or more agents to be encapsulated and one or more polymers in solution to produce one or more microcapsules, optionally separating said microcapsules from solution, and applying said one or more microcapsules to a substrate such that said microcapsules fixedly adhere to said substrate.

The invention also relates to a method of providing an additive agent to a primary agent comprising providing a composition comprising a substrate having adhered thereto one or more microcapsules comprising one or more polymers encapsulating one or more agents to be delivered, such that said one or more agents to be delivered are released upon exposure to appropriate conditions, and supplying appropriate conditions for release of said one or more agents.

DETAILED DESCRIPTION OF THE INVENTION

Figure 1:
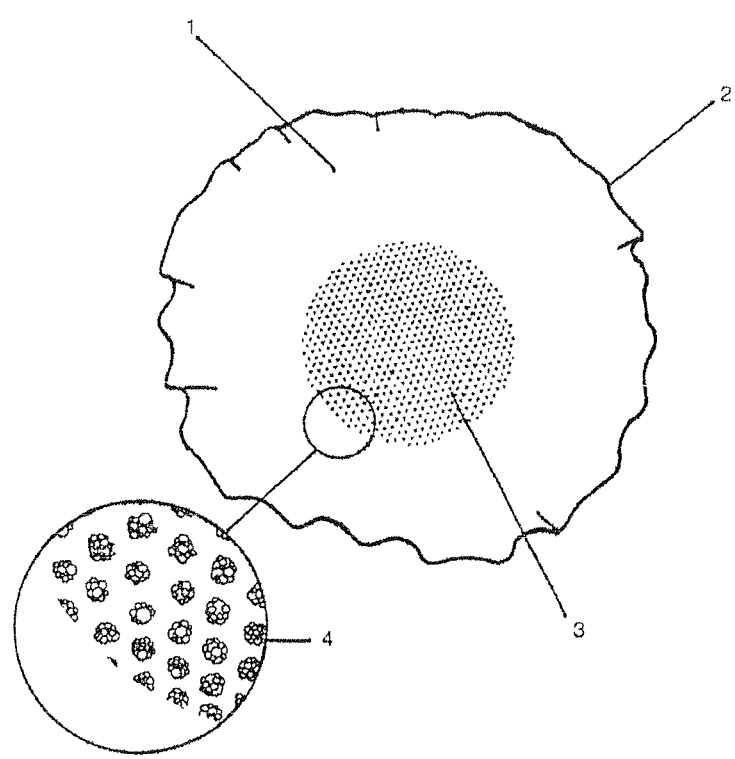
FIG. 1 shows an example of a typical basket-type drip coffee maker filter 1 having a multiplicity of microcapsule clusters affixed to the bottom surface 3 within the pleated filter basket. As shown in magnified view 4 the clusters of microcapsules are arranged in such a pattern as to allow the normal filtration of water to prevent an overflow condition through the spaces between clusters and a sufficient volume of flavored additive to prepare an entire pot of coffee (e.g., 12 cups).

As described herein, the invention relates to a microencapsulated delivery system, composition or method in which one or more agents to be delivered are encapsulated in small capsules (e.g., microcapsules), and the capsules are applied or adhered to one or more surfaces of a substrate. The encapsulated agent is latently released upon exposure to appropriate conditions, i.e., conditions which cause the rupture or permeation of the capsules. In one embodiment "appropriate conditions" excludes tactile breakage of the microcapsules, i.e., breakage of the microcapsule by physically pressing, abrading, puncturing or squeezing.

In a preferred embodiment breakage of the microcapsule is performed utilizing one or more specific matching conditions to avoid accidental, premature or unintended release of the encapsulated agent. As used herein, specific matching conditions are conditions particularly tailored to cause relatively immediate release of the encapsulated agent. For example, specific conditions of pH and temperature may be required to cause relatively immediate release of some microcapsules, while specific aqueous and temperature conditions may be required to cause relatively immediate release of others. In preferred embodiments the release is caused by one or more dynamic condition changes. In other preferred embodiments release of the agent is caused by a chemical reaction involving the microcapsule and the substrate or environment.

Virtually any useful agent can be incorporated into a capsule (e.g., a microcapsule) for use in the invention. Suitable agents may include, but are not limited to, one or more flavorings, aromas/fragrances, colorings, pharmaceuticals, herbal remedies, vitamins, minerals, medicinal preparations, cosmetics or cosmetic agents, chemical and analytical agents, food and beverage additives and any other agent for which latent release would be beneficial or useful. The agent can be in liquid or solid form, provided that the agent does not prevent the formation of microcapsules as described further herein. In some embodiments it may be preferable to include the agent in a concentrated and/or hydrophobic form, for example as an oil-based extract. A single agent can be encapsulated alone, or combinations of agents can be encapsulated within the same or different microcapsules.

For example, flavorings may include natural or artificial flavoring agents including, but not limited to, cinnamon, hazelnut, almond, nutmeg, vanilla, sweeteners (e.g., sucrose, corn syrup, fructose, and dextrose), spices, fruit flavorings, vinegar, alcoholic agents (e.g., Baileys®, Kahlua®, Chambord®, Frangelico®, vodka, rum, etc.), chocolate, gravy and poultry- and meat-flavored juices, milk, cream and the like. Colorings may include, but are not limited to, natural or artificial food grade dyes.

Examples of pharmaceuticals and medicinal preparations suitable for use in the invention include any orally administrable agent including, but not limited to, vaccines, pain relievers, antibiotics, cough suppressants, cold remedies, antacids, etc. Suitable herbal remedies and dietary supplements include, but are not limited to, acacia, ginseng, ginkgo, Echinacea, flaxseed, flaxseed oil, Hoodia, lycopene, lutein, and coenzyme Q10. Vitamins and minerals may include without limitation vitamins A, B (thiamine, riboflavin, niacin, pantothenic acid, biotin, vitamin B-6, vitamin B-12 and folate), C, D, E, and K, iron, calcium, magnesium, selenium, and zinc. Food and beverage additives suitable for use in the invention include, for example, antioxidants, antimicrobial agents, emulsifiers, and stabilizers. Compositions of the invention are particularly well suited to microdosing applications.

Appropriate cosmetics or cosmetic agents for use in the invention include, but are not limited to, organic and synthetic agents such as Retinol®, skin care agents such as creams and lotions, teeth cleaning and whitening agents, nail care agents, perfumes, lipsticks, sunscreens, hair color, mascara, and chemical peels. Suitable chemical and analytical agents include, but are not limited to, sliver, chlorine, iodine, potassium nitrate, proteins (e.g., antibodies, receptors, etc.), *Roccella tinctoria*, acids, bases, nucleic acids and the like.

Depending upon the agent to be encapsulated, suitable encapsulation methods will be selected as known to the skilled artisan. For example, complex or simple coacervation, spray drying, Wurster coating, fluidized bed or co-extrusion, and ultrasonic cavitation are but a few technologies appropriate for use depending on cost, application, physical characteristics and compatibility with the material to be encapsulated. Generally the encapsulation process will entail encapsulating the agent to be delivered (the "inner phase material") within a polymer capsule comprising one or more polymers (the "outer phase material").

The selection of the appropriate polymer or combination of polymers will depend on the agent to be encapsulated and the substrate to which the encapsulated agent is to be affixed/adhered. Suitable polymers may include, but are not limited to, natural or synthetic polymers, gums, starches, lipids, pectins, and agars. For example, gelatin (e.g., bovine or porcine gelatin), gum arabic, carageenan, locust bean gum, pectin are examples of suitable outer phase materials for use in the invention. In some embodiments the polymer will have a bloom strength of 250 or greater. For food, beverage, nutraceutical, pharmaceutical or cosmetic usage the outer phase material(s) must be acceptable under the appropriate regulatory regime (GRAS, DSHEA, FDA, etc.).

Generally speaking the agent to be encapsulated is mixed with a solution of the outer phase material(s), and small droplets are formed which comprise the inner phase material(s) entrapped within the outer phase material(s) using methods known in the art. A single microcapsule can contain one or more inner phase materials. Microcapsules are formed which are typically from about 50 to about 2500 µm in diameter; smaller or larger diameter microcapsules may also be useful depending upon the volume of agent to be delivered.

If needed, further polymerization can be achieved by means of several common cross-linking agents such as gluteraldehyde. Further cross-linking is usually not necessary with most additives if the outer-phase material used forms a solid at room temperature.

The formed microcapsules are separated from any liquid suspension and applied to an appropriate substrate. The microcapsules are of sufficient structural strength to allow for many different methods of application to the substrate, including, but not limited to, inkjet printing, offset printing, screen printing through a pattern mask and spray coating. The wet capsule slurry is then dried, causing the shells of the microcapsules to harden sufficiently to be handled without causing release of the encapsulated inner-phase components.

The microcapsules can be applied to any suitable substrate, including paper, waxed paper, plastic (e.g., hard or soft plastics such as plastic bags and plastic wrap), glass, styrene, fiber (e.g., cloth), filter paper, tea bags, coffee flavor pods and discs, aluminum foil and the like. The substrate surface may be unmodified or may be modified prior to application of the microcapsules to improve the adherence of the microcapsules to the substrate. For example, the substrate can be etched by chemical or mechanical means to allow for an improved bond between the microcapsules and the substrate. Alternatively or additionally, a suitable binding agent can be applied to the surface of the substrate to adhere or affix the microcapsules to the surface.

The microcapsules can be affixed in systematic or random patterns covering all or a portion of one or more surfaces of the substrate. For example, the microcapsules can be affixed in a graphic pattern such as a product name, company logo, grill "sear marks" or other pleasing design. In this embodiment it may be desirable to add one or more dyes to the microcapsules and to apply the microcapsules in multiple applications, optionally using masking technologies, to facilitate creation of a specific pattern. Alternatively the microcapsules can be applied to only a portion of the substrate consistent with the intended use of the embodiment. For example, microcapsules may be applied only to the lower interior sides and bottom of drinking cup, integrated delivery cup or indicator cup embodiments.

Microcapsules can be applied such that a given substrate ultimately contains only a single type of outer phase material containing one or more inner phase materials. Alternatively more than one type of outer phase material can be applied containing one or more inner phase material in each outer phase. For example, a single outer phase material encapsulating chlorine can be applied to a substrate, and another, distinct outer phase material encapsulating a chlorine scavenger can also be applied to the substrate. The different outer phase materials can have the same or different environmental triggers. For example, one outer phase material affixed to a substrate can be triggered by contact with a liquid, while another outer phase material affixed on the substrate can be triggered by a threshold temperature. Alternatively one outer phase material affixed to a substrate can be triggered by a threshold temperature while another outer phase material affixed to the substrate can be triggered at a higher or lower threshold temperature. In this way the release of the encapsulated agents can be controlled (e.g., released at the same time or release at different times in response to different triggers).

At the time of delivery, release of the inner phase material(s) can be accomplished using one or more suitable release or trigger methods. Many release or trigger methods may be envisioned provided that the method provides conditions that will cause the microcapsules to fail to a sufficient degree to release the encapsulated agent. For example, suitable triggers include, but are not limited to, physical disruption of the microcapsules (e.g., tactile pressure), pH change, temperature, presence of moisture, expansion of inner phase material, contraction of outer phase material, microwave energy, and/or chemical reaction. For example an acidic beverage such as orange juice contacting an outer phase material that dissolves or destabilizes in the presence of a weak acid would cause release of the inner phase material(s); this is an example of a specific matching condition. Alternatively, the introduction of a fluid having a sufficient temperature differential, hot or cold, relative to the encapsulated ingredient would cause the inner phase material to expand beyond the confines of the capsule envelope, ultimately resulting in a catastrophic loss of membrane integrity. Certain embodiments of the invention may require the microcapsule to rupture to release the agent(s) contained therein, but other embodiments may require only permeation of the microcapsule to a point of equilibrium with the surrounding fluid or environment.

In one preferred embodiment of the present invention the substrate consists of a section of filtration paper with sufficient porosity for brewing heated beverages such as coffee or tea, having the ability to retain the organic solid but permeable to the filtrated liquid. A coffee filter used in drip-type automatic coffee makers is a typical example of such a filter. The filter, being "cup" or "basket" shaped, having a round flat bottom and pleated sides is used as the substrate for one application of the flavor delivery system.

Figure 2:
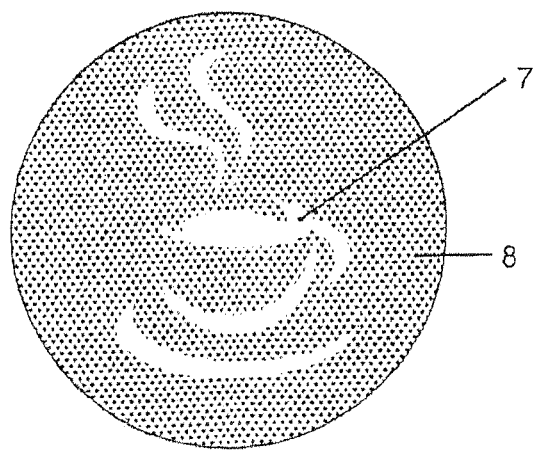
FIG. 2 shows a typical flavor disc that has been masked to demonstrate how an image or corporate logo might be "printed" within the microcapsule pattern. The negative image 7 is masked during the screen printing of the capsule clusters 8, thus forming an image within the microcapsule pattern. Colorized images or logos are also possible using multi-colored microcapsules and employing common screen-printing overlay techniques.
Figures 3, 4:
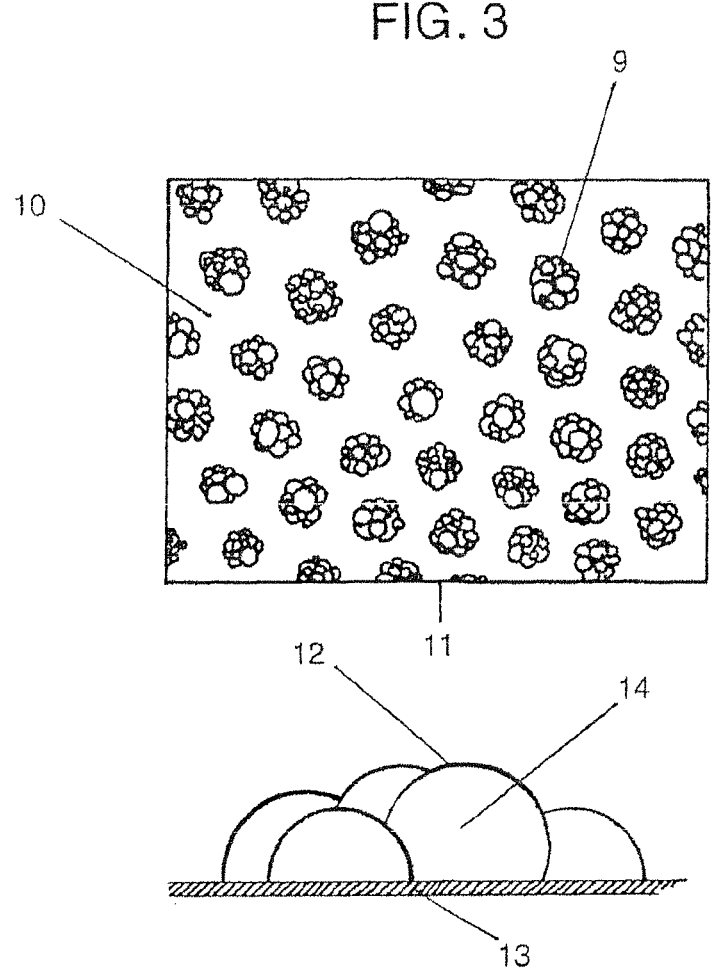
FIG. 3 shows a magnified view of an arrangement of microcapsule clusters 9 and the spaces 10 between them on the surface of a paper filter substrate 11.
FIG. 4 shows a significantly magnified profile view of the same microcapsule clusters 12 on a paper substrate 13, clearly showing the individual liquid-filled gelatin microspheres 14.
Figure 5:
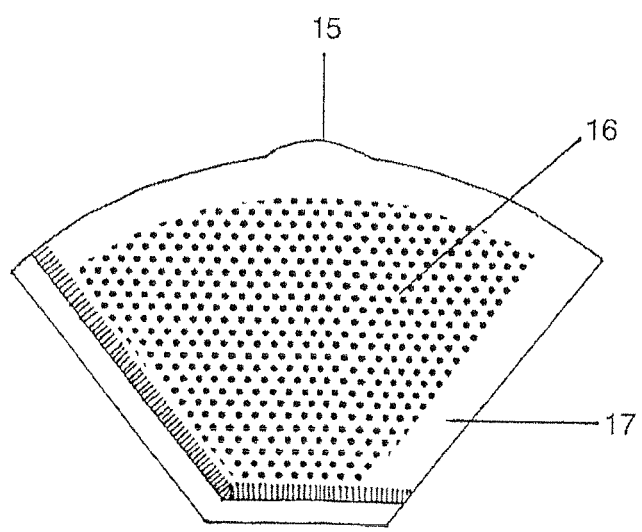
FIG. 5 is a diagram of an alternative configuration of the coffee filter using a "cone-shape" filter basket or Melitta®-type filter (15). The microcapsule clusters 16 are affixed on the interior of the filter envelope but due to the translucency of the filter material 17 are visible from the outside.

In one preferred embodiment, the finished capsules are "silk-screened" onto a coffee-filter substrate to form a pattern of clustered microcapsules as shown in FIG. 1. This pattern is used to permit some of the water to flow through the filter unimpeded by the microcapsules to prevent an overflow condition during the brewing process, e.g., until the majority of microcapsules have dissolved to such a degree as to allow the water to pass through the filter membrane where the microcapsules were previously deposited. These patterns may be altered to form text, images and logos if desired (FIG. 2). The pattern may also be modified to increase or decrease the relative strength of the additive. FIG. 3 shows a magnified view of the microcapsules formed into patterned clusters, while FIG. 4 depicts a close-up view of the individual fluid-filled microcapsules in aggregate clusters as they appear on the filter material surface. Similar results may be obtained using different filter geometries such as cone-type or "Melitta" filters (FIG. 5), provided the microcapsules are within the internal portion of the filter material that becomes wetted during the brewing cycle. This also applies to "tea bags" and other flavor extraction methods using heated fluid or steam as the primary preparation process. This invention can also be used to impart additives to other beverages such as hot apple cider, hot chocolate or any other heated beverage that would benefit from a latent flavoring technique by means of application of the microencapsulated ingredients onto a filter or paper substrate during preparation or onto the internal walls of the serving container from which the beverage may be consumed.

As an alternative to purchasing large and sometimes expensive volumes of flavored coffee such as a "pound of hazelnut" that may not be used quickly enough to avoid the remainder becoming stale, this embodiment of the invention allows the user to flavor one pot or cup at a time using standard unflavored coffee roasts. For instance, if the filters as described herein were provided in a multiplicity of flavors such as cinnamon, hazelnut or almond, then the user need only to purchase a single unflavored roast coffee and would be able to make a pot of the desired flavor without having to purchase three large volumes of pre-flavored coffee that may not be completely consumed within the recommended shelf-life period of the coffee. In another example, the user may obtain filters that contain microencapsulated extracts of superior coffees such as "Kona" or other richer, more expensive blends. Rather than buying the more expensive roast in quantity, the user may impart the essence of the more expensive roast into lower grades of coffee such as that available in retail cans.

Figure 6:
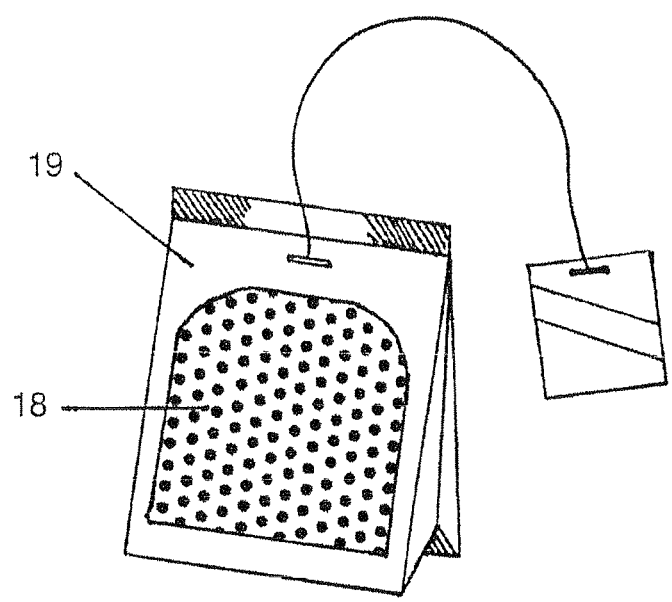
FIG. 6 is a diagram of a conventional tea bag with microcapsule clusters that are capable of containing medicinal ingredients, herbal supplements, flavorings or other beneficial additives 18 affixed to the inside surface of the semi-transparent, fluid-permeable envelope 19.

In other embodiments the invention can be used to add most any additive to almost any beverage. For example, one can create a "spice filter" specifically for use with ciders. Spices are imparted to the cider as it passes through an appropriately flavored filter. In addition, many otherwise perishable ingredients that would normally be unsuitable for storage at room temperature would be protected from spoilage within the barrier provided by the microencapsulation. In another example, the invention encompasses a filter envelope of similar configuration to be immersed in water to prepare or steep tea. The interior of the "teabag" envelope is prepared with a similar microcapsule delivery system, thus imparting flavors, herbal remedies such as chamomile or medicinal substances such as aspirin to the tea upon contact with the heated water as shown in FIG. 6.

The following examples are intended to illustrate certain embodiments of the invention and are not intended to be limiting. The teachings of all websites and documents cited herein are incorporated herein by reference in their entirety.

EXAMPLES

Example 1: Coffee/Beverage Filter

In one aspect of the invention the microencapsulated delivery system is embodied in a beverage (e.g., coffee) filter.

In this example complex coacervation is the preferred method of encapsulation, although many other suitable methods are known, including, but not limited to, spray drying, Wurster coating, fluidized bed or co-extrusion. Cinnamon will be used as the illustrative additive although many others such as, for example, hazelnut, almond, Baileys, etc. may be used. A quantity of high bloom porcine or bovine gelatin having a 250 bloom strength or greater (i.e., the preferred first polymer) is dissolved in a volume of water. An equal quantity of gum arabic (i.e., the co-polymer) is dissolved in an equal volume of water. The pH of the sols will be approximately (6.0-8.0) at 25 degrees centigrade.

Figure 7:
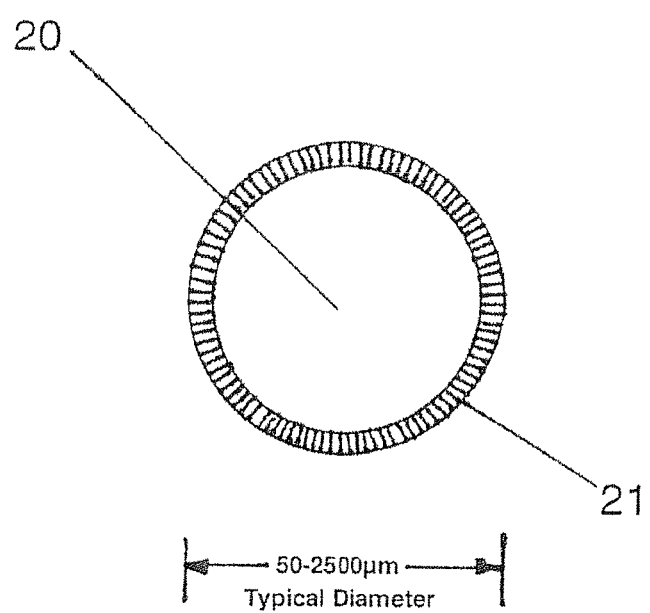
FIG. 7 shows a diagram of an individual, single-core, single-walled, liquid filled microcapsule showing both internal 20 and external phases 21.

Next, a suitable quantity of the concentrated additive, preferably an oil-based extract, (i.e., the "inner-phase" material) is added to either of the aforementioned sols to form an emulsion. With moderate agitation, the second sol is then added to the first sol/emulsion. Once both are mixed, the agitation will begin to form droplets of the oil extract rather than form a layer of oil or hydrophobic material. Once the droplets are divided into a suitable size (typically between 50-2500 μm in diameter or larger), the stirring is continued but not so fast as to decrease, or so slow as to increase, the size of the droplets. The pH is then reduced to approximately 4.5, and the temperature of the material is increased to approximately 45 degrees centigrade. When the pH reaches 4.5, there will be a noticeable "clouding" of the solution. This flocculation of the polymer indicates that the coacervate is forming around the oil droplets; that is, a layer of gelatin and gum-arabic (i.e., the outer-phase material or complex polymer) is forming a shell around the oil-based additive. Once the shell is of sufficient thickness and all of the available coacervate has enveloped the oil phase, then the sol is rapidly cooled in a bath of chilled water to about 5 degrees centigrade. At this point, the liquid complex-polymer wall solidifies, trapping the additive within the newly formed microcapsule (see, e.g., FIG. 7). The pH is then adjusted to above 6.0 to prevent further coacervation. Adjustments of pH can be achieved with weak solutions (5-10%) of acetic acid or sodium hydroxide, depending upon the pH change required.

If needed, further polymerization can be achieved by means of several common cross-linking agents such as gluteraldehyde. However, in this particular instance a sufficient but relatively weak cross-linking occurs due to the naturally occurring aldehydes (cinnamaldehyde) already present in the cinnamon flavoring. Further cross-linking is usually not necessary with most other additives if the outer-phase material used forms a solid at room temperature. The microcapsules are then placed in a centrifuge or separation funnel, rinsed with water, and drained. A slurry of relatively uniform, spherical, liquid-filled microcapsules is thus formed. These microcapsules may be dehydrated to a free-flowing powder and stored or may be used as is; they may also be stored in the slurry state. The outer capsule will increase the shelf-life of the additive, protecting flavor and other efficacious characteristics by providing a barrier against contamination or microbial infestation until the release of the inner-phase material.

Figure 8:
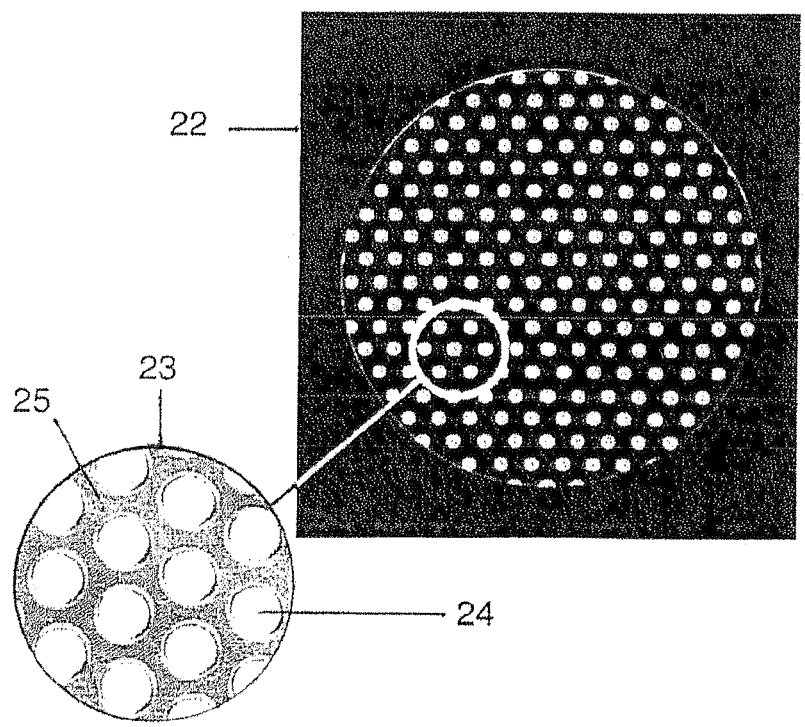
FIG. 8 shows a teflon-coated polypropylene screen mask 22 used to "screen-print" the clusters onto the substrate. The magnified view 23 shows detail of the perforated material. The size of the perforations 24 and thickness of the perforated material 25 may vary to accommodate adjustment of additive delivery volumes. Of course, the microcapsules may be applied to the substrate surface by several alternative methods including but not limited to, inkjet, spraying, laminating and many others.

Next, the slurry may be applied to a filter-paper substrate using a perforated mask or "screen" (see, e.g., FIG. 8). The process is very similar to silk-screening except that the perforations are of a size that will allow the microcapsules to pass through the mask to be affixed or adhered to the substrate below. In one embodiment the perforations will typically be from about 0.066" to about 0.125" in diameter in order to permit formation of suitable clusters of microcapsules on the substrate with sufficient additive to flavor an entire pot (12 cups) of coffee. A suitable masking material is Teflon-coated, perforated HDPE. After the capsule slurry is drawn across the perforated mask using a squeegee device, the mask is removed and the filter paper is allowed to dry. The outer-phase material will generally adhere to the substrate surface upon drying. However, if necessary, a separate binder of starch, albumin or other edible adherent may be used. Once dehydrated, the capsules will harden with sufficient wall strength to be handled normally without inadvertent breakage of the otherwise frangible capsules. The capsules can be colorized prior to application to the substrate and applied in a decorative pattern, text, image or logo (see, e.g., FIG. 2) when printed onto the filter. Alternatively all or a portion of the microcapsules and/or substrate can be colorized after application of the microcapsules to the substrate. The filter is now ready for use.

The filter is then placed into an automatic drip coffee maker and filled with the appropriate amount of ground coffee of a presumably unremarkable grade. The coffee is brewed in the usual way. As the hot water begins to filter through the coffee, it begins to dissolve the gelatin shells of the microcapsules affixed to the filter wall, thus slowly releasing the flavoring additive into the coffee flow. The empty microcapsule shells are mostly dissolved and remain in the filter with the spent coffee bean granules. The cinnamon flavoring has now been successfully imparted into the coffee beverage. The filter and its contents may now be discarded. In addition to flavorings, other characteristic-enhancing materials may also be incorporated into the filter as described herein. These may include, but are not limited to, materials for the removal of chlorine and other contaminants, pH modifiers to improve taste, or additives to enhance or change the appearance or physical characteristics of the brewed beverage.

Example 2: Flavor Disc

In one aspect of the invention the microencapsulated delivery system is embodied in a flavor disc.

Figure 9:
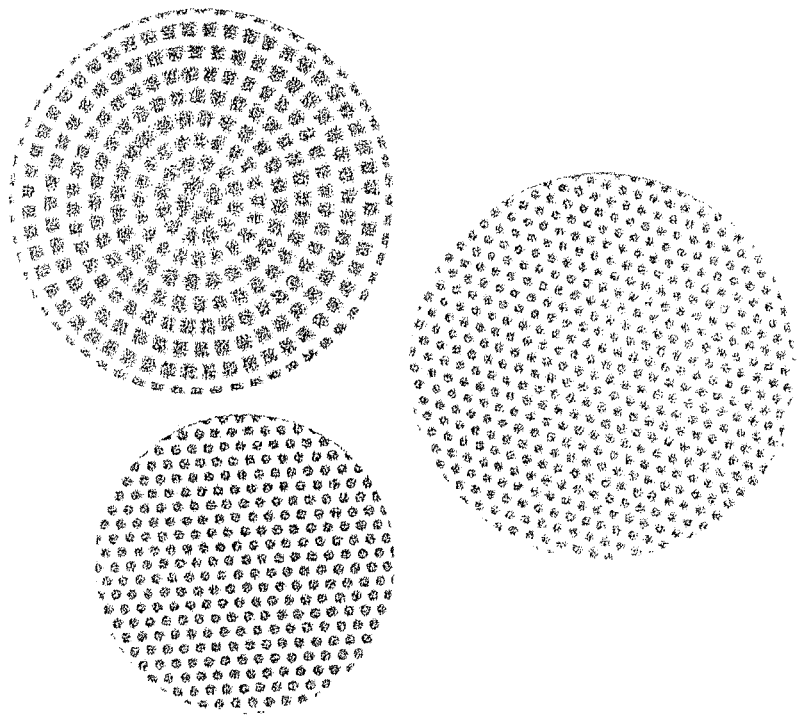
FIG. 9 illustrates several typical circular "Flavor Disc" configurations in a variety of microcapsule patterns and disc sizes. The disc shape is preferred but any other geometry or cluster pattern may be used provided that its combined surface-area (front and back) is sufficient to support the necessary volume of encapsulated material for delivery. The discs as shown are single-sided.

In this example the microencapsulated delivery system is prepared identically as in Example 1 with the exception that the substrate is a paper disc or other desired shape having a pattern or coating of the microencapsulated agent applied thereto. FIG. 9 shows several examples of disc-shaped pattern configurations with 0.066" to 0.125" diameter clusters across the entire surface of the discs. Delivery of the encapsulated agent in this embodiment Could simply entail immersing the prepared flavor disc in the beverage prior to consumption for a sufficient period of time to allow the microcapsules to dissolve, thus delivering the interior phase component(s). These discs could be configured to also deliver flavors, fragrances, characteristic modifiers, colorants, vitamins and medicinal ingredients to a variety of liquid beverages, hot or cold.

Example 3: Cosmetic and Cosmeceutical Applicator Discs

In one aspect of the invention the microencapsulated delivery system is embodied in cosmetic or cosmeceutical applicator such as an applicator disc.

In this example the microencapsulated delivery system is prepared identically as in Example 2 with the exception that the inner-phase material constitutes a cosmetic or medicinal preparation such a Retinal or other topical dermal treatment to be applied to the skin. The microcapsules will release the internal-phase material through tactile pressure, pH change, body temperature, presence of perspiration, or external environmental, conditions thus delivering the internal component in the dosage desired under predetermined release circumstances over a specified time period.

Example 4: Cooking Bag

In one aspect of the invention the microencapsulated delivery system is embodied in a bag suitable for use in the oven, steamer, crock pot, microwave or the like.

In this example the microencapsulated delivery system is prepared identically as in Example 1 with the exception that the substrate is a heat-resistant polymer bag or envelope having a surface prepared in such a way that the microcapsules may be securely affixed thereto. An example of this preparation is to etch the surface by chemical or mechanical means to allow for a mechanical bond between the plastic surface and the microcapsule outer-phase material. In the event the microcapsules are prepared prior or independent of the manufacturing process, an additional binder can be used to affix the capsules if needed. The purpose of the embodiment is to allow the latent release of food additives such as color, aroma, vitamins, flavorings or other ingredients or additives that may be suited to this application. A food item is placed in the bag prior to cooking by any convenient and appropriate methods such as convection, boiling or microwave. The microcapsules are affixed in a pattern to the interior of the envelope-bag. They will release their inner-phase components under predetermined conditions which may be a certain range of temperature, the presence of microwave energy, pH change or any other factor that could be used to initiate the rupture of the microcapsules. Upon release, the capsules will deliver flavor, aroma, coloring or even a "grill searing pattern" to the surface of the article of food in accordance with the pattern in which they were affixed to the interior of the cooking bag. This embodiment is particularly useful in the manufacture of pre-prepared frozen foods, especially those cooked by microwave that are otherwise unable to achieve desirable characteristics imparted by conventional oven cooking.

Example 5: Flavor Cup

In one aspect of the invention the microencapsulated delivery system is embodied in a cup or bowl.

Figure 10:
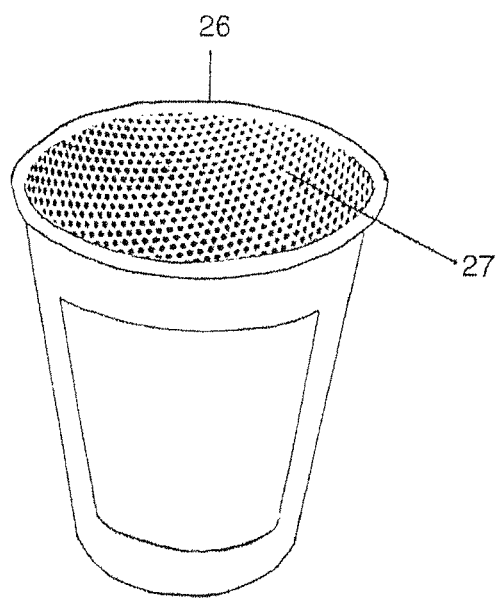
FIG. 10 illustrates a typical disposable beverage cup 26 with microcapsule clusters containing a concentrated ingredient or additive affixed to the interior wall 27 in a typical pattern. However, the capsules need not be in "clusters" in this instance, as the fluid does not pass through the vessel; therefore there is no need to have "spaces" between microcapsule aggregates. The capsules may be affixed in a single contiguous coating if desired, and the pattern thickness may be increased or decreased to adjust additive volume and potency.

In this example the microencapsulated delivery system is also prepared identically as shown in Example 1 with the exception that the substrate is a bowl, drinking cup or other food or beverage container. Ideally, the vessel will be a disposable, one-time use container for use with hot or cold food or beverages having affixed to one or more interior surfaces of said container microcapsules arranged in a pattern or contiguous layer for the purpose of imparting the agent to whatever food or fluid is introduced into the vessel. FIG. 10 shows the interior wall of a common hot beverage cup (e.g., a paper coffee cup) with a pattern of "concentrated instant coffee" microcapsule clusters that have been screen-printed onto the coated paper interior surface. The microcapsule shells are of sufficient strength to allow the cups to be stored in a "nested" stack without inadvertent or premature release of the inner-phase materials due to tactile breakage. However, once a liquid, hot or cold is introduced into the container, the capsules will dissolve, thus releasing their contents into the fluid. It is foreseen that this embodiment could be modified for use with most any other type of container including those constructed of materials other than paper such as plastics, styrene, glass, natural fiber and many others. Use of plastic, glass or similar materials may require surface activation to securely affix the microcapsules to the substrate as described in EXAMPLE 4. The capsules may contain, for example, the ingredients that make up "instant coffee," requiring only the addition of water to create the beverage. The capsules may also contain extracts of high-grade roast coffees. If a lower grade of coffee beverage is introduced into the cup, the high grade extracts will be released, thus enhancing the flavor and aroma of the lesser grade blend. Alternatively, the capsules may only contain a flavoring such as cinnamon or even a beverage condiment such as a milk substitute, sugar or both. In the latter case, coffee would then be added, releasing the milk substitute and sugar combination and creating what is generally recognized as a "regular" cup of the beverage. "Pre-prepared" cups of this configuration would be particularly useful in coffee vending machines or where coffee is served in an inconvenient location such as by a flight attendant aboard an aircraft, saving significant time, space and inventory.

Example 6: Integrated Delivery Platform (IDP) Cup

In one aspect of the invention the microencapsulated delivery system is embodied in a cup for integrated delivery of a pharmaceutical.

In this example the microencapsulated delivery system is prepared identically as shown in Example 5. However the utility of this configuration is intended for a variety of pharmaceutical applications. In this embodiment, the cup may be used to orally deliver a broad spectrum of medicinal preparations such as vaccines, vitamins, pain relievers, drugs or any other pharmaceutical compound appropriate for this type of delivery. This would be particularly beneficial for those individuals that are unable or otherwise reluctant to ingest pharmaceuticals in pill or tablet form. This invention would also facilitate the administering of vitamins and other medicinal preparations to children as the drug or supplement can be covertly delivered within a beverage more appetizing and familiar to the child. The child's beverage of choice would then become the carrier medium once the latent release of the encapsulated material has occurred. Some practical and beneficial applications would include but are not limited to, children and adult vitamins, cold remedies, teeth whitening systems, dentifrices, aspirin cups, Alka-Seltzer® cups, disposable vaccine cups and energy drinks.

Example 7: Indicator Cup

In one aspect of the invention the microencapsulated delivery system is embodied in an indicator cup.

In this example the microencapsulated delivery system is also prepared identically as shown in Example 5, but the encapsulated agents are suitable for indicating the presence or absence of specific chemicals, elements or compounds by means of an indicative color change reaction. In concept this embodiment is similar to conventional pH litmus strips but functions by means of encapsulation of solutions or saturated particles containing indicators such as *Roccella Tinctoria*. This indication can be accomplished, for example, in three ways:

1. A color change caused by an indicator or reagent incorporated into the internal or external phase of the affixed microcapsules. Indicative color change would occur through permeation, rather than dissolution of the capsule causing the capsules to change color while remaining intact and affixed to the wall of the container.
2. A change in the color of the introduced liquid via release of the indicating agent into the liquid by dissolution of the external phase of the microcapsules affixed to the internal wall.
3. A change in color caused by close proximity or intimate contact to the microcapsule. A representative example of this is a thermally-induced color change. While the affixed capsules remain intact and no permeation of the capsule membrane occurs, a thermo-chromic leuco dye indicator may be incorporated into either the inner or outer phase of the microcapsule making the capsule sensitive to change in temperature. These capsules may be affixed to the outer surface of the container if general proximity to the liquid is sufficient. However, this embodiment provides additional utility if heat transfer speed is critical and intimate contact with the liquid is required. Unlike other indicators of this type, segregation is maintained, thus preventing the indicator from interacting or contaminating the solution within the disposable container.

This embodiment has particular utility in circumstances where the presence or absence of a chemical must be determined and the validity of the sample must be verified at the time of collection. One example of this would be a disposable urinalysis drug testing device having a plurality of microcapsules affixed to the interior wall of a paper or plastic collection cup with a percentage of the capsules containing an anti-body dye conjugate and the remainder containing an appropriately calibrated thermo-chromic indicator solution. Upon collection, a color change would occur in the conjugate capsules in the presence of a pre-determined compound or chemical such as THC, a cannabinoid. A similar color change would be evident in the thermally sensitive capsules ensuring that the sample is at human body temperature and was indeed collected immediately from the test subject. Multiple types of indicator capsules may be incorporated into a single cup for a variety of separate tests including those that would otherwise be incompatible processes for simultaneous testing of the same sample in-situ. Many other applications of this embodiment are foreseen and can be configured to indicate potency, concentration, pH or any other instant chemical analysis suited to this method. Uses include, but are not limited to, drug testing, urinalysis, ketosis testing, pregnancy testing, water safety analysis, pH testing, chemical analysis or any application where an inexpensive, instant, and disposable indicating container would be desirable.

Example 8: Water Safety Cup

In one aspect of the invention the microencapsulated delivery system is embodied in a water safety cup.

In this example the microencapsulated delivery system is prepared identically as shown in Example 5 but is intended to provide a means of increasing the potability of water. Various water sanitizing agents such as chlorine, silver and iodine are effective against most harmful bacteria found in untreated water and can be encapsulated for use within the scope of this invention. Of the three sanitizers previously listed, chlorine is the least expensive and most desirable to use. However, it must be delivered in an accurate dosage based on the exact volume of water to be treated which is generally regarded as impractical to implement outside of controlled conditions. However, because the water safety cup of the invention contains a known volume of fluid, a precise measure of chlorine sufficient to sanitize the entire quantity may be administered at the time the cup is filled. The microcapsules affixed to the internal wall of the container containing a particulate form of chlorine will dissolve upon contact with water. Sanitization is immediate and the one-time use container is disposable. Alternatively, microcapsules having a latent release time greater than that of the primary sanitizing microcapsules may be affixed to the container wall simultaneously. These secondary capsules may contain chlorine scavengers such as potassium nitrate (saltpeter) or other flavor enhancers to remove any unpleasant after-taste remaining from the initial purification process. This example contemplates configurations with particular utility for the military, international travel, hospitality industry, camping, hiking and other outdoor activities where water is available but potability is in question.

What is claimed is:

1. A method of preparing a composition comprising mixing one or more agents to be encapsulated and one or more polymers in solution to produce one or more microcapsules, separating said microcapsules from solution, and printing said one or more microcapsules to a substrate in a systematic pattern such that said microcapsules fixedly adhere to said substrate, wherein said one or more agents are released from said microcapsules upon dissolution of the microcapsules following exposure to a solvent.

2. The method of claim 1, wherein the systematic printed pattern comprises an image or a logo.

3. A composition comprising a substrate having adhered thereto in a systematic printed pattern one or more microcapsules comprising one or more polymers encapsulating one or more agents to be delivered, such that said one or more agents to be delivered are released upon dissolution of the microcapsules following exposure to a solvent, wherein the microcapsules do not require a threshold temperature for dissolution of the microcapsules and release of the one or more agents to be delivered.

4. The method of claim 1, wherein the microcapsules do not require a threshold temperature for dissolution of the microcapsules and release of the one or more agents to be delivered.

5. A method of providing an additive agent to a primary agent comprising providing a composition comprising a substrate having adhered thereto in a systematic printed pattern one or more microcapsules comprising one or more polymers encapsulating one or more agents to be delivered, such that said one or more agents to be delivered are released upon dissolution of the microcapsules following exposure to a solvent, and supplying the solvent for release of said one or more agents, wherein the microcapsules do not require a threshold temperature for dissolution of the microcapsules and release of the one or more agents to be delivered.

* * * * *